United States Patent [19]

Bowler et al.

[11] 4,321,275

[45] Mar. 23, 1982

[54] METHOD OF INDUCING LUTEOLYSIS USING 16-ARYLOXY-17,18,19,20-TETRANOR-PROSTANOIC ACID DERIVATIVES

[75] Inventors: Jean Bowler; Neville S. Crossley, both of Macclesfield, England

[73] Assignee: Imperial Chemical Industries Limited, London, England

[21] Appl. No.: 474,608

[22] Filed: May 30, 1974

Related U.S. Application Data

[63] Continuation of Ser. No. 248,717, Apr. 28, 1972, abandoned.

[30] Foreign Application Priority Data

May 11, 1971 [GB] United Kingdom .............. 14139/71

[51] Int. Cl.$^3$ ........................................... A61K 31/557
[52] U.S. Cl. ..................................... 424/317; 424/308; 424/343; 542/414; 542/416; 542/420; 542/426; 260/347.2; 260/347.3; 260/347.4; 560/9; 560/10; 560/11; 560/45; 560/53; 560/56; 560/55; 562/427; 562/429; 562/426; 562/452; 562/462; 562/463; 562/465; 562/466; 568/37; 568/42; 568/47; 568/330; 568/631
[58] Field of Search .......... 260/473 GA, 520, 468 D, 260/488 CD; 424/308, 317

[56] References Cited

U.S. PATENT DOCUMENTS 3,833,612  9/1974  Wendler et al. .................... 424/305

*Primary Examiner*—Henry R. Jiles
*Assistant Examiner*—Bernard Dentz
*Attorney, Agent, or Firm*—Cushman, Darby & Cushman

[57] ABSTRACT

The disclosure relates to novel 17,18,19,20-tetranor-prostanoic acid derivatives having prostaglandin-type properties, to a method for their manufacture, and also to pharmaceutical or veterinary compositions containing said novel derivatives and a method of inducing luteolysis in an animal host by use of said novel derivatives.

4 Claims, No Drawings

METHOD OF INDUCING LUTEOLYSIS USING 16-ARYLOXY-17,18,19,20-TETRANOR-PROSTANOIC ACID DERIVATIVES

This application is a continuation of Ser. No. 248,717, filed Apr. 28, 1972 and now abandoned.

This invention relates to new cyclopentane derivatives, and in particular it relates to new cyclopentane derivatives which are analogues of the naturally occurring compounds known as prostaglandin $F_{2\alpha}$ and prostaglandin $E_2$, showing a similar spectrum of pharmacological properties and being useful for similar purposes. The relative potency of the new compounds, however, in respect of the particular pharmacological effects shown is different from that of the above naturally occurring prostaglandins, and in particular they are more potent as luteolytic agents than the corresponding natural prostaglandins. That is to say, the prostaglandin $F_{2\alpha}$ analogues of the present invention are more potent than natural prostaglandin $F_{2\alpha}$, and the prostaglandin $E_2$ analogues of the present invention are more potent than natural prostaglandin $E_2$. The new compounds are, in a similar way, more potent as stimulants of uterine smooth muscle than the corresponding natural prostaglandins $F_{2\alpha}$ and $E_2$, and the prostaglandin $E_2$ analogues of the invention are particularly valuable in this respect. The new compounds are therefore advantageous when used as contraceptives, for the termination of pregnancy or for control of the oestrus cycle, as hypotensives or for the relief of bronchospasm. The new compounds of the invention are also useful for addition to semen intended for artificial insemination of domestic animals, the success rate of insemination being thereby increased, especially in pigs.

The cyclopentane derivatives described in this specification will be named as derivatives of prostanoic acid of the formula shown below and numbered as shown:

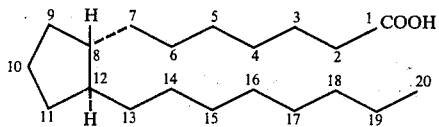

According to the invention there is provided a prostanoic acid derivative of the formula:

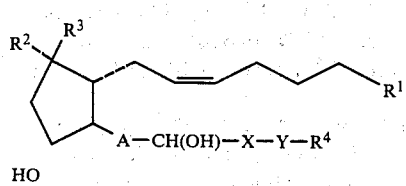

wherein $R^1$ is a hydroxymethyl or carboxy radical, an alkoxycarbonyl radical of up to 11 carbon atoms or an alkoxycarbonyl radical of 2 or 3 carbon atoms which bears as substituent a β- or γ-dialkylamino radical wherein each alkyl radical is of 1 to 4 carbon atoms, or a β- or γ-pyrrolidino, piperidino or morpholino radical; either $R^2$ is a hydroxy radical or an alkanoyloxy radical of 1 to 4 carbon atoms and $R^3$ is a hydrogen atom, or $R^2$ and $R^3$ together form the oxo radical; A is an ethylene or vinylene radical; X is an alkylene radical of 1 to 3 carbon atoms bearing as substituents 0, 1 or 2 alkyl radicals, each of 1 to 3 carbon atoms; Y is an oxygen or sulphur atom, a sulphinyl (—SO—) radical or an alkylimino (—NAlkyl—) radical of up to 4 carbon atoms; and $R^4$ is an aryl, benzyl or furfuryl radical, which is unsubstituted or which is substituted by hydroxy or halogen atoms, nitro or phenyl radicals, alkyl, alkenyl, halogenoalkyl, alkoxy, alkenyloxy or acylamino radicals of 1 to 4 carbon atoms or dialkylamino radicals wherein each alkyl is of 1 to 3 carbon atoms; which compound contains 0 or 1 alkyl radicals of up to 4 carbon atoms on carbon atoms 2, 3 or 4; and for those compounds wherein $R^1$ is a carboxy radical, the pharmaceutically acceptable salts thereof.

A suitable value for $R^1$ when it is an alkoxycarbonyl radical of up to 11 carbon atoms is, for example, the methoxycarbonyl, ethoxycarbonyl, n-butoxycarbonyl or n-decyloxycarbonyl radical.

A suitable value for $R^2$ when it is an alkanoyloxy radical of 1 to 4 carbon atoms is, for example, the acetoxy or propionyloxy radical.

A suitable value for X when it is an alkylene radical of 1 to 3 carbon atoms bearing as substituents 0, 1 or 2 alkyl radicals, each of 1 to 3 carbon atoms is, for example a methylene, ethylene or trimethylene radical bearing 0, 1 or 2 methyl substituents, for example the methylene, ethylidene, isopropylidene and trimethylene radicals.

A suitable value for Y when it is an alkyleneimino radical of up to 4 carbon atoms is, for example, the methylimino ($CH_3$—N<) radical.

A suitable value for A is the trans-vinylene radical.

A suitable value for $R^4$ when it is an aryl radical, optionally substituted, is for example a phenyl or naphthyl radical optionally substituted.

Suitable halogen atom substituents in $R^4$ are, for example, chlorine, bromine or fluorine atoms. Suitable alkyl, alkoxy, alkenyl or alkenyloxy substituents of 1 to 4 carbon atoms in $R^4$ are, for example methyl, t-butyl, allyl, methoxy or allyloxy radicals. Suitable halogenoalkyl substituents of 1 to 4 carbon atoms in $R^4$ are, for example chloroalkyl or fluoroalkyl radicals, for example trifluoromethyl radicals. Suitable dialkylamino radicals wherein each alkyl is of 1 to 3 carbon atoms, which may be substituents in $R^4$ are, for example, dialkylamino radicals wherein the two alkyl radicals are the same, for example the dimethylamino radical.

Suitable substituted aryl radicals are for example, chlorophenyl, chloronaphthyl, bromophenyl, fluorophenyl, tolyl, xylyl, methylnaphthyl, t-butylphenyl, methylchlorophenyl, trifluoromethylphenyl, hydroxyphenyl, methoxyphenyl, methoxynaphthyl, biphenylyl, dimethylaminophenyl and tetrahydronaphthyl radicals.

Preferred aryl radicals contain not more than two substituents as defined above. Particular values for $R^4$ are, therefore, the phenyl, benzyl, furfuryl, 1-naphthyl, 2-naphthyl, 2-, 3- and 4-chlorophenyl, 4-bromophenyl, 2-, 3- and 4-fluorophenyl, 2,3-, 2,4-, 2,5-, 2,6-, 3,4- and 3,5-dichlorophenyl, 2-, 3- and 4-tolyl, 2,3-, 3,4- and 3,5-xylyl, 4-t-butylphenyl, 3-allylphenyl, 3-trifluoromethylphenyl, 4-hydroxyphenyl, 2-, 3- and 4-methoxyphenyl, 4-biphenylyl, 3-dimethylaminophenyl, 2-chloro-4-methylphenyl, 1-chloro-2-naphthyl, 4-chloro-2-naphthyl, 6-methyl-2-naphthyl, 6-methoxy-2-naphthyl and 5,6,7,8-tetrahydro-2-naphthyl radicals.

A suitable value for the alkyl radical of up to 4 carbon atoms which may be present as a substituent on carbon atom 2, 3 or 4 is, for example the methyl radical.

Examples of base-addition salts are the ammonium, alkyl-ammonium containing 1 to 4 alkyl radicals each of 1 to 6 carbon atoms, alkanolammonium containing 1 to 3 2-hydroxyethyl radicals, and alkali metal salts, for example the triethylammonium, ethanolammonium, diethanolammonium, sodium and potassium salts.

It will be observed that the compounds of the formula I contain at least five asymmetric carbon atoms, namely carbon atoms 8, 9, 11, 12 and 15, the configurations at four of which, 8, 9, 11 and 12 are specified in formula I, and that carbon atoms 2, 3 and 4 may also be asymmetrically substituted, so that it is clear that such compounds can exist in at least two optically active forms. It is to be understood that the useful properties of the racemate may be present to differing extents in the optical isomers, and that this invention relates to the racemic form of the compounds of formula I and any optically active form which shows the above useful properties, it being a matter of common general knowledge how the optically active forms may be obtained, and to determine their respective biological properties.

It is also to be understood that the above definition encompasses both C-15 epimers and that in all chemical formulae shown hereafter in this specification, the same fixed stereochemistry at C-8, 9, 11 and 12 as that shown in formula I is implied.

Although both C-15 epimers of a compound of the invention possess desirable pharmacological properties, that epimer which is more polar on thin layer chromatography is the more active, for example in the luteolytic test, and the more polar C-15 epimers are therefore preferred.

A preferred group of cyclopentane derivatives of the invention, because of their high luteolytic or smooth muscle stimulant properties, comprises those compounds wherein $R^4$ is a chlorophenyl, fluorophenyl, trifluoromethylphenyl or unsubstituted naphthyl radical, especially those compounds wherein $R^1$ is the carboxy, methoxycarbonyl or hydroxymethyl radical, and particularly those compounds wherein $R^4$ is the 3- or 4-chlorophenyl, 2- or 4-fluorophenyl, 3-trifluoromethylphenyl or unsubstituted naphthyl radical. A particularly preferred subgroup comprises those compounds wherein $R^1$ is the carboxy, methoxycarbonyl or hydroxymethyl radical, $R^2$ is the hydroxy radical and $R^3$ is a hydrogen atom, or $R^2$ and $R^3$ together form the oxo radical, A is the vinylene radical, X is the methylene or isopropylidene radical, Y is an oxygen atom and $R^4$ is the 3- or 4-chlorophenyl, 2- or 4-fluorophenyl, 3-trifluoromethylphenyl or 2-naphthyl radical, optionally bearing a methyl substituent on carbon atom 2.

Particular preferred compounds of the invention are 16-(4-fluorophenoxy)-9α,11α,15-trihydroxy-17,18,19,20-tetranor-5-cis-13-trans-prostadienoic acid, methyl 16-(4-fluorophenoxy)-9α,11α,15-trihydroxy-17,18,19,20-tetranor-5-cis-13-trans-prostadienoate, 16-(2-fluorophenoxy)-9α,11α,15-trihydroxy-17,18,19,20-tetranor-5-cis-13-trans-prostadienoic acid, 16-(4-chloropheoxy)-9α,11α,15-trihydroxy-17,18,19,20-tetranor-5-cis-13-trans-prostadienoic acid, methyl 16-(4-chlorophenoxy)-9α,11α,15-trihydroxy-17,18,19,20-tetranor-5-cis-13-trans-prostadienoate, 16-(4-chlorophenyl)-9α,11α,15-trihydroxy-17,18,19,20-tetranor-5-cis-13-trans-prostadienol, 16-(3-chlorophenoxy)-9α,11α,15-trihydroxy-17,18,19,20-tetranor-5-cis-13-trans-prostadienoic acid, methyl 16-(3-chlorophenoxy)-9α,11α,15-trihydroxy-17,18,19,20-tetranor-5-cis-13-trans-prostadienoate, 16-(3-chlorophenoxy)-9α,11α,15-trihydroxy-2-methyl-17,18,19,20-tetranor-5-cis-13-trans-prostadienol, 9α,11α,15-trihydroxy-16-(3-trifluoromethylphenoxy)-17,18,19,20-tetranor-5-cis-13-trans-prostadienoic acid, 9α,11α,15-trihydroxy-16-(2-naphthyloxy)-17,18,19,20-tetranor-5-cis-13-trans-prostadienoic acid, 16-(4-chlorophenoxy)-9α,11α,15-trihydroxy-16,16-dimethyl-17,18,19,20-tetranor-5-cis-13-trans-prostadienoic acid and 16-(4-chlorophenoxy)-11α,15-dihydroxy-9-oxo-17,18,19,20-tetranor-5-cis-13-trans-prostadienoic acid.

The cyclopentane derivatives of the invention may be manufactured by methods known in themselves for the manufacture of chemically analogous compounds. Thus, the following processes for the manufacture of the cyclopentane derivative of the formula I, are provided as further features of the invention:

(a) for those compounds wherein $R^1$ is a carboxy radical, the hydrolysis of a compound of the formula:

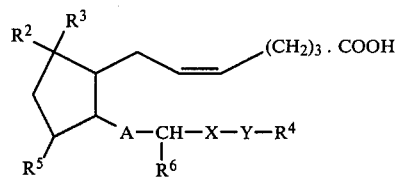

II or of a mixed anhydride thereof, wherein A, X, Y, $R^2$, $R^3$ and $R^4$ have the meanings stated above, and $R^5$ and $R^6$ are each a tetrahydropyran-2-yloxy radical, or an acyloxy radical of 1 to 6 carbon atoms, whereafter when a salt is required the product is reacted with a base; or (b) for those compounds wherein $R^1$ is an alkoxycarbonyl radical of 1 to 11 carbon atoms, the reaction of an acid of the formula:

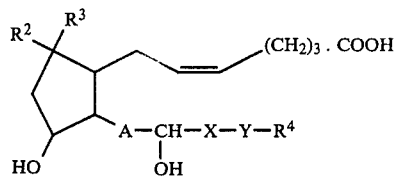

III wherein A, X, Y, $R^2$, $R^3$ and $R^4$ have the meanings stated above, with a diazoalkane of the formula $R^7.N_2$, wherein $R^7$ is an alkyl radical of 1 to 11 carbon atoms; or (c) for those compounds wherein $R^1$ is an alkoxycarbonyl radical of 1 to 11 carbon atoms, the reaction of a salt, for example the silver salt, of an acid of the formula II, with an alkyl halide of 1 to 11 carbon atoms, for example the alkyl iodide; or (d) for those compounds wherein $R^1$ is the hydroxymethyl radical and Y is the oxygen or sulphur atom, or an alkylimino radical, the reduction of an ester of the formula I wherein $R^1$ is an alkoxycarbonyl radical, for example an alkoxycarbonyl radical of 1 to 11 carbon atoms, for example with a complex metal hydride, for example lithium aluminium hydride, or (e) for those compounds wherein Y is the sulphinyl radical, the oxidation of a thio-compound of the formula:

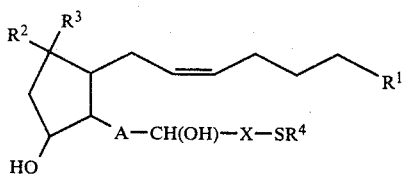

wherein $R^1$, $R^2$, $R^3$, $R^4$, A and X have the meanings defined in claim 1, for example with sodium periodate.

A suitable mixed anhydride is a mixed anhydride with a lower alkanoic acid, for example a lower alkanoic acid of up to 8 carbon atoms, for example acetic acid.

The hydrolysis in process (a) may be carried out under either acidic or basic conditions, for example in aqueous acetic acid, or in an aqueous or alcoholic solution of an alkali metal carbonate, for example potassium carbonate in methanol, and it may be carried out at ambient temperature or at an elevated temperature of up to 60° C.

The starting material of the formula II wherein A is a vinylene radical, and Y is an oxygen or sulphur atom, used in the process of the invention may be obtained by reaction of the known aldehyde IV (Ac=acetyl or p-phenylbenzoyl) with a phosphonate of the formula $(CH_3O)_2P^+O.^-CH.CO.X.Y.R^4$ (V) (which is prepared from dimethyl methylphosphonate and an ester of the formula $R^4.Y.X.COO$ alkyl, in the presence of butyllithium), or with a phosphorane of the formula $Ph_3P:CH.CO.X.Y.R^4$ (which is prepared from triphenylphosphine and a compound of the formula $R^4.Y.X.COCH_2I$), to give an unsaturated ketone VI. The ketone VI is reduced with zinc borohydride to the corresponding unsaturated alcohol VII, and the protecting acyl group is then removed with potassium carbonate in methanol to give a diol VIII. The diol VIII is protected as a bis-tetrahydropyranyl ether and the lactone ring is then reduced with di-isobutyl aluminium hydride to give a lactol X, or alternatively the diol VIII is reduced with diisobutyl aluminium hydride to give a triol which may be acylated and selectively hydrolysed to give the lactol bis-ester (X, $R^5=R^6$=acyloxy). The lactol X is reacted with the phosphonium ylide anion obtained from (4-carboxybutyl)triphenylphosphonium bromide and a strong base, to give a carboxylic acid of the formula II.

The starting material of the formula II wherein A is an ethylene radical, and Y is an oxygen or sulphur atom, used in the process of the invention, may be obtained by hydrogenating an unsaturated ketone VI in the presence of 5% palladium-on-carbon catalyst, or with nickel boride, to give a saturated ketone XI, and repeating the procedure outlined above using the saturated ketone XI in place of the unsaturated ketone VI.

The starting material of the formula II wherein $R^2$ is an alkanoyloxy radical may be obtained from the corresponding compound wherein $R^2$ is a hydroxy radical by acylation with an acid anhydride in pyridine to give a 9-ester-1-mixed anhydride.

The starting material of the formula I, II or III, wherein $R^2$ and $R^3$ together form the oxo radical, may be obtained from the corresponding starting material of the formula II, wherein $R^2$ is hydroxy and $R^3$ is hydrogen, by oxidation with Jones' reagent (chromic acid in acetone), followed, as required, by hydrolysis of the tetrahydropyranyl protecting groups and esterification of the carboxylic acid group.

It is, of course, to be understood that an optically active compound of the invention may be obtained either by resolving the corresponding racemate, or by carrying out the above-described reaction sequences starting from an optically active intermediate, for example from an optically active aldehyde of the formula IV (Ac=acetyl or p-phenylbenzoyl).

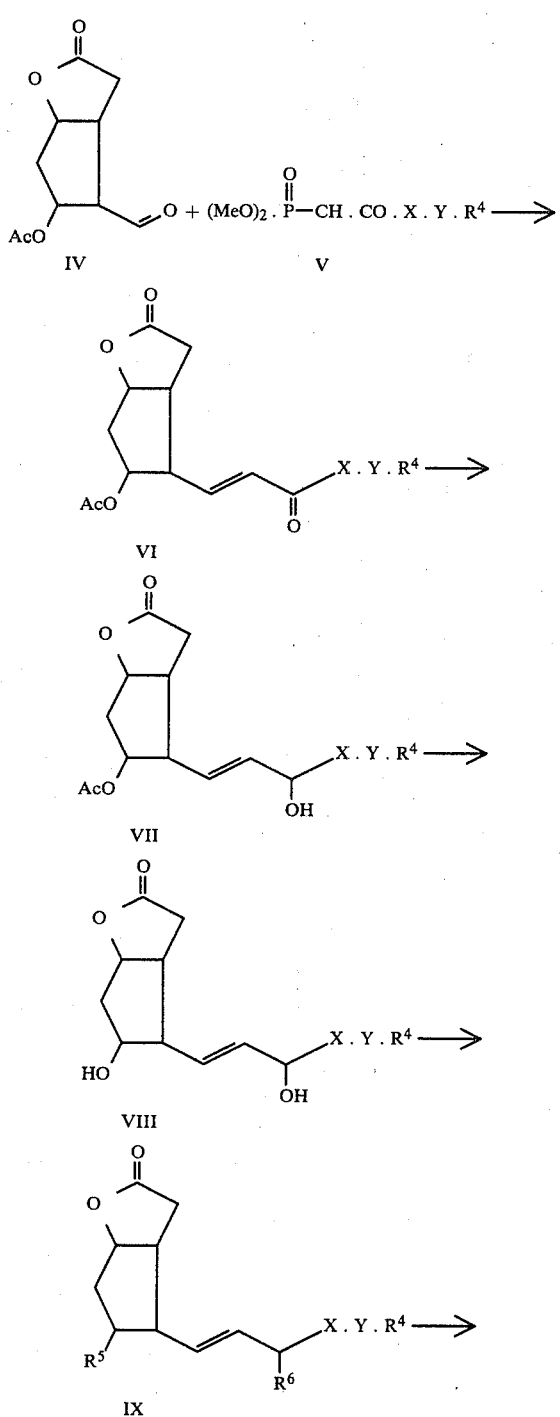

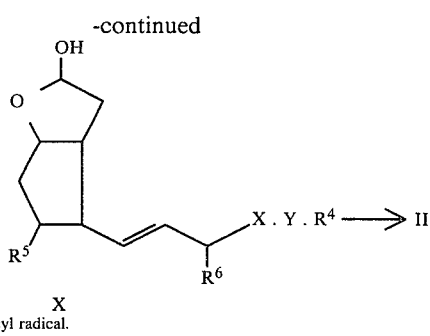

X

Ac represents an acyl radical.

As stated above, the compounds of the invention possess a profile of pharmacological properties which differs from that of the naturally occurring prostaglandins $F_{2\alpha}$ and $E_2$. Thus, for example, 16-(4-fluorophenoxy)-9α,11α,15-trihydroxy-17,18,19,20-tetranor-5-cis-13-trans-prostadienoic acid is approximately 200 times as active as prostaglandin $F_{2\alpha}$ in a luteolytic test in the hamster (oral dosing), and about 10 times the smooth muscle stimulant activity of prostaglandin $F_{2\alpha}$.

Also as stated above, the compounds of the invention are useful, for example, for the induction of labour in childbirth, and for this purpose are used in the same way as it is known to use the naturally-occurring prostaglandins $E_1$ and $E_2$, that is to say, by administering a sterile, substantially aqueous solution containing from 0.01 to 10 μg./ml., preferably 0.01 to 1 μg./ml. of active compound, by intravenous infusion until labour commences. Also, for this purpose, the compounds of the invention may be used in combination, or concurrently, with a uterine stimulant, for example oxytocin, in the same way that it is known to use prostaglandin $F_{2\alpha}$ in combination, or concurrently with oxytocin for the induction of labour.

When a compound of the invention is to be used for the control of the oestrus cycle in animals, it may be used in combination, or concurrently, with a gonadotrophin, for example PMSG (pregnant mare serum gonadotrophin) or HCG (human chorionic gonadotrophin) to hasten the onset of the next cycle.

Thus, according to a further feature of the invention there is provided a pharmaceutical or veterinary composition comprising a prostanoic acid derivative of the invention, together with a pharmaceutically or veterinarily acceptable diluent or carrier.

The compositions may be in a form suitable for oral administration, for example tablets or capsules, in a form suitable for inhalation, for example an aerosol or a solution suitable for spraying, in a form suitable for parenteral administration, for example sterile injectable aqueous or oily solutions or suspensions, or in the form of a suppository, suitable for anal or vaginal use. As stated above, when the compound of the invention is to be used for the induction of labour in childbirth, a preferred composition of the invention is a sterile, substantially aqueous, injectable solution.

The compositions of the invention may be prepared by conventional means, and may incorporate conventional excipients.

The invention is illustrated, but not limited, by the following Examples:

EXAMPLE 1

A solution of 9α-hydroxy-16-phenoxy-11α,15-bis(tetrahydropyran-2-yloxy)-17,18,19,20-tetranor-5-cis-13-transprostadienoic acid (120 mg.) in 1.5 ml. of a 2:1 mixture of acetic acid and water, was stirred at 50° C. for 4 hours. The solvents were evaporated, the residue was dissolved in dilute aqueous sodium bicarbonate solution (2 ml.) and the solution was extracted with ethyl acetate (3×2 ml.) and the extracts were discarded. The aqueous solution was acidified to pH 3–4 with 2 N aqueous oxalic acid and the acidified solution was extracted with ethyl acetate (4×5 ml.). The ethyl acetate extracts were washed with a 1:1 mixture of saturated brine and water, and were then dried. After evaporation of the ethyl acetate, the residue consisted of a mixture of the C-15 epimers of 9α,11α,15-trihydroxy-16-phenoxy-17,18,19,20-tetranor-5-cis-13-trans-prostadienoic acid. Thin-layer chromatography on silica gel plates, supplied commercially by Merck of Darmstadt, using a mixture of benzene:dioxan:acetic acid (20:10:1) as the developing solvent, separated the C-15 epimers, having $R_F$ values of 0.3 and 0.4, respectively. (Throughout this Example $R_F$ values refer to silica gel plates supplied commercially by Merck of Darmstadt, and the spots were detected either by fluorescence, or by spraying the plates with a solution of ceric ammonium nitrate in sulphuric acid). The n.m.r. spectrum of each isomer (in deuterated acetone) showed the following characteristic bands (δ values):

5.6–6.1, broad multiplet, 5 aromatic protons 4.2–4.8, broad multiplets, 4 olefinic protons 2.9–3.8, broad multiplets, 3H, $\underline{H}$-C-O and 4 exchangeable protons The bis-tetrahydropyranyl ether used as starting material may be prepared as follows:

n-Butyl lithium (69 ml. of a 1.2 M solution in hexane) was added to a solution of dimethyl methylphosphonate (10.3 g.) in dry tetrahydrofuran at −78° C. in an atmosphere of nitrogen. After 10 minutes, a solution of phenoxyacetylchloride (4.1 g.) in dry tetrahydrofuran (20 ml.) was added dropwise, and the mixture was stirred for 4 hours at −78° C. The reaction mixture was neutralised with acetic acid and the solvents were removed under reduced pressure. The residue was shaken with a mixture of ether (100 ml.) and water (20 ml.), and the organic phase was separated and washed with brine. The solution was dried, the solvents were evaporated and the residue was distilled in a bulb distillation apparatus at an oven temperature of 160° C. and 0.1 mm. pressure, to give dimethyl 2-oxo-3-phenoxypropylphosphonate.

A solution of dimethyl 2-oxo-3-phenoxypropylphosphonate (1.01 g.) in dry 1,2-dimethoxyethane (20 ml.) at −78° C. was treated with n-butyl-lithium (2.75 ml. of a 1.2 M solution in hexane), and the mixture was stirred for 15 minutes. To this mixture was added a solution of 4β-formyl-2,3,3aβ,6aβ-tetrahydro-2-oxo-5α-(p-phenylbenzoyloxy)cyclopenteno[b]furan (1.95 g.) in 1,2-dimethoxyethane (10 ml.), and after 1 hour the reaction mixture was neutralised with glacial acetic acid and all solvents were removed by evaporation under reduced pressure below 35° C. The residue was chromatographed on Florisil using solutions of ethyl acetate in methylene chloride as eluant, to yield the unsaturated ketone product as a white solid. [$R_F$=0.6 (1:1 ethyl acetate/benzene)].

To a solution of the unsaturated ketone (500 mg.) in dry 1,2-dimethoxyethane (20 ml.) at 0° C. was added 1.5 ml. of a 0.5 M solution of zinc borohydride in 1,2-dimethoxyethane. The mixture was stirred at room temperature for 30 minutes, then saturated sodium hydrogen tartrate solution was added until effervescence ceased. Ethyl acetate (100 ml.) was added, the organic layer was separated, washed with a 1:1 mixture of saturated brine and water, then dried. The solvents were evaporated to give a mixture of epimeric unsaturated alcohols. [$R_F$=0.3 (1:1 ethyl acetate/benzene)].

The mixture of epimeric unsaturated alcohols (500 mg.) was stirred vigorously for 2 hours with finely powdered anhydrous potassium carbonate (140 mg.) in methanol (10 ml.). 1 N Hydrochloric acid (2.1 ml.) was added, followed by ethyl acetate (50 ml.). The organic layer was separated, washed successively with saturated sodium bicarbonate solution and saturated brine, and dried, and the solvents were evaporated. The residue was chromatographed on Florisil (20 g.). Elution with ether removed by-products, and subsequent elution with ethyl acetate gave a mixture of the C-15 epimeric diols [$R_F$=0.2 (ethyl acetate)].

To a solution of the epimeric diols (316 mg.) in methylene chloride (3 ml.) under an atmosphere of nitrogen were added successively redistilled 2,3-dihydropyran (1.2 ml.) and a solution of anhydrous toluene-p-sulphonic acid in tetrahydrofuran (0.1 ml. of a 1% solution).

After 10 minutes, pyridine (3 drops) were added, followed by ethyl acetate (50 ml.). The solution was washed successively with saturated sodium bicarbonate solution and saturated brine, and was dried. Evaporation of the solvents gave a mixture of epimeric bis-tetrahydropyranyl ethers as a clear oil. [$R_F$=0.6 (ethyl acetate)].

To a solution of the epimeric bis-tetrahydropyranyl ethers (420 mg.) in dry toluene (10 ml.) under an atmosphere of nitrogen at −78° C. was added 1 ml. of a 2.2 mmole/ml. solution of di-isobutyl aluminium hydride in toluene. After 15 minutes the reaction was quenched by the dropwise addition of methanol (3 ml.) and after a further 15 minutes at room temperature a mixture of 1:1 saturated brine/water (25 ml.) was added, and the mixture was extracted with ethyl acetate (3×50 ml.). The extract was washed with saturated brine, and dried, and the solvents were evaporated to give a mixture of epimers of 2,3,3a$\beta$,6a$\beta$-tetrahydro-2-hydroxy-4$\beta$-[4-phenoxy-3-(tetrahydropyran-2-yloxy)-1-trans-butenyl]-5$\alpha$-(tetrahydropyran-2-yloxy)cyclopenteno[b]furan. [$R_F$=0.4 (1:1 ethyl acetate/benzene)].

Finely powdered (4-carboxybutyl)triphenylphosphonium bromide (1.11 g.) was heated to 100° C. under vacuum for 1 hour. The evacuated reaction vessel was filled with an atmosphere of dry nitrogen, the solid was dissolved in dimethylsulphoxide (5 ml.) and the solution was cooled to room temperature. To this solution was added dropwise 2.35 ml. of a 2 M solution of methanesulphinylmethyl sodium in dimethyl sulphoxide followed by a solution of the mixture of epimers of the cyclopenteno[b]furan bis-tetrahydropyranyl ether (400 mg.) in a mixture of dimethylsulphoxide (10 ml.) and benzene (2 ml.). The solution was stirred for 3 hours, and the solvent was removed by evaporation under reduced pressure at a temperature below 40° C. The residue was shaken with water (10 ml.) and ethyl acetate (10 ml.) and the aqueous phase was separated, extracted with ethyl acetate (2×10 ml.) and the extracts discarded. The aqueous solution was acidified to pH 3–4 with 2 N aqueous oxalic acid, and extracted with a mixture of equal parts of ether and petroleum ether (b.p.40°–60° C.) (5×10 ml.). The organic phase was separated, washed with saturated brine and was dried. Evaporation of the solvents gave 9$\alpha$-hydroxy-16-phenoxy-11$\alpha$,15-bis(tetrahydropyran-2-yloxy)-17,18,19,20-tetranor-5-cis-13-trans-prostadienoic acid as a clear oil. [$R_F$=0.5 (ethyl acetate)].

EXAMPLE 2

The process described in Example 1 was repeated, using the appropriate phosphonate reagent, to give the compounds shown below. The products were identified by n.m.r. spectroscopy and are characterized below either by $R_F$ value on thin layer chromatography, or by accurate mass measurement by mass spectrometry of either the molecular ion or the (M+-methyl) ion, whichever is more appropriate, of the tetra (trimethylsilyl) derivative, which is prepared by adding to the compound to be mass measured bis-trimethylsilyl-trifluoroacetamide containing 1% trimethylchlorosilane (Regisil-trade mark) and leaving the mixture for 1 hour. In some cases, the phosphonate reagent, or the unsaturated ketone intermediate have been characterised and appropriate data for these compounds are also given.

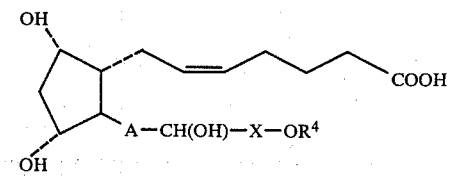

| No. | R⁴ | A | X |
|---|---|---|---|
| 1 | phenyl | —CH:CH— | —CH₂— |
| 2 | phenyl | —CH:CH— | —CH(CH₃)— |
| 3 | phenyl | —CH:CH— | —C(CH₃)₂— |
| 4 | phenyl | —CH:CH— | —(CH₂)₃— |
| 5 | benzyl | —CH:CH— | —CH₂— |
| 6 | 2-naphthyl | —CH:CH— | —CH₂— |
| 7 | 4-chlorophenyl | —CH:CH— | —CH₂— |
| 8 | 4-chlorophenyl | —CH₂CH₂— | —CH₂— |
| 9 | 3-chlorophenyl | —CH:CH— | —CH₂— |
| 10 | 2-chlorophenyl | —CH:CH— | —CH₂— |
| 11 | 2,4-dichlorophenyl | —CH:CH— | —CH₂— |
| 12 | 4-bromophenyl | —CH:CH— | —CH₂— |
| 13 | 4-fluorophenyl | —CH:CH— | —CH₂— |
| 14 | 4-tolyl | —CH:CH— | —CH₂— |
| 15 | 3-tolyl | —CH:CH— | —CH₂— |
| 16 | 4-t-butylphenyl | —CH:CH— | —CH₂— |
| 17 | 3-trifluoromethylphenyl | —CH:CH— | —CH₂— |
| 18 | 4-methoxyphenyl | —CH:CH— | —CH₂— |
| 19 | 2-methoxyphenyl | —CH:CH— | —CH₂— |
| 20 | 4-biphenylyl | —CH:CH— | —CH₂— |

| No. | Isomer* | Mass spectrum Found | Calculated | Phosphonate b.p. (°C./mm.) | Enone m.p. (°C.) |
|---|---|---|---|---|---|
| 1 | mp | M⁺ = 678.3610 | 678.3625 | 178–185/0.05 | 155–158 |
|   | lp | M⁺ = 678 |  |  |  |
| 2 | mp | M⁺—CH₃ = 677.3540 | 677.3545 | 175/0.2 | — |

-continued

| No. | Isomer* | Mass spectrum Found | Mass spectrum Calculated | Phosphonate b.p. (°C./mm.) | Enone m.p. (°C.) |
|---|---|---|---|---|---|
|  | lp | $M^+ = 692$ | 692 |  |  |
| 3 | mixed | $M^+{-}CH_3 = 691.3660$ | 691.3703 | 130/0.1 | — |
| 4 | mp | $M^+ = 706.3921$ | 706.3938 | 166–168/0.1 | 120–122 |
|  | lp | $M^+ = 706$ |  |  |  |
| 5 | mixed | $M^+ = 692.3753$ | 692.3781 | 170/0.1 | 99–101 |
| 6 | mp | $M^+ = 728.3744$ | 728.3781 | m.p. = 85–86° C. | 185–187 |
| 7 | mp | $M^+{-}CH_3 = 697.2948$ | 697.3001 | 170–173/0.1 | 132–135 |
|  | lp | $M^+ = 712$ | 712 |  |  |
| 8 | mp[a] | $M^+ = 714.3399$ | 714.3391 | 170–173/0.1 | 132–135 |
|  | lp[a] | $M^+ = 714$ |  |  |  |
| 9 | mp | $M^+{-}CH_3 = 697.2297$ | 697.3000 | 180/0.2 | — |
|  | lp | $M^+ = 712$ | 712 |  |  |
| 10 | mp | $M^+ = 712.3216$ | 712.3235 | 174–178/0.1 | 129–132 |
|  | lp | $M^+ = 712$ |  |  |  |
| 11 | mp | $M^+{-}CH_3 = 731.2599$ | 731.2609 | — | 136–138 |
| 12 | mixed | $M^+{-}CH_3 = 741.2485$ | 741.2497 | — | — |
| 13 | mp | $M^+ = 696.3468$ | 696.3529 | — | 162 |
|  | lp | $M^+ = 696$ |  |  |  |
| 14 | mixed | $M^+ = 692.3738$ | 692.3781 | 164/0.05 | 149 |
| 15 | mp | $M^+ = 692.3752$ | 692.3781 | 180/0.5 | 140–141 |
|  | lp | $M^+ = 692$ |  |  |  |
| 16 | mixed | $M^+ = 734.4213$ | 734.4251 | — | — |
| 17 | mp | $M^+ = 746.3467$[b][c] | 746.3499 |  | 115–117 |
|  | lp |  |  |  |  |
| 18 | mp | $M^+ = 708.3717$ | 708.3731 | — | — |
|  | lp | $M^+ = 708$ |  |  |  |
| 19 | mp | $M^+ = 708.3710$ | 708.3731 | — | — |
|  | lp | $M^+ = 708$ |  |  |  |
| 20 | mp | $M^+ = 754.3944$ | 754.3938 | m.p. = 63–64° C. | — |
|  | lp | $M^+ = 754$ |  |  |  |

*mp = more polar, lp = less polar isomer on silica gel thin layer chromatography.
[a]products synthesised from respectively the more polar and less polar enol intermediates.
[b]$R_F = 0.45$ after 2 runs on silica gel t.l.c. with 5% acetic acid in ethyl acetate.
[c]$R_F = 0.50$ after 2 runs on silica gel t.l.c. as for [b].

In the manufacture of compounds 8, wherein A is an ethylene radical, the unsaturated ketone intermediate is reduced to the saturated ketone as follows:

The more polar epimer (epimers at C-3 of the butenyl side-chain) of 4β-(4-p-chlorophenoxy-3-hydroxybut-1-enyl)-2,3,3aβ,6aβ-tetrahydro-2-oxo-5α-(p-phenylbenzoyloxy)cyclopenteno[b]furan (360 mg.) was dissolved in ethanol (25 ml.) and the solution was added to nickel boride, previously prepared from nickel acetate (620 mg.) and sodium borohydride (2.5 ml. of a 1 M solution). The mixture was shaken with hydrogen for 3 hours and was then filtered, and the filtrate was evaporated to dryness to give 4β-(4-p-chlorophenoxy-3-hydroxybutyl)-2,3,3aβ,6aβ-tetrahydro-2-oxo-5α-(p-phenylbenzoyloxy)cyclopenteno[b]furan, $R_F=0.4$ (50% ethyl acetate in toluene). The saturated ketone was then used, in place of the unsaturated ketone, in the remainder of the process described in Example 1.

EXAMPLE 3

To a solution of the more polar C-15 epimer of 16-(4-chlorophenoxy)-9α,11α,15-trihydroxy-17,18,19,20-tetranor-5-cis-13-trans-prostadienoic acid (15 mg.) in methanol (1 ml.) at 0° C. was added an excess of a solution of diazomethane in ether. After 10 minutes the solvents were evaporated to give a single C-15 epimer of methyl 16-(4-chlorophenoxy)-9α,11α,15-trihydroxy-17,18,19,20-tetranor-5-cis-13-trans-prostadienoate as a clear oil, $R_F=0.3$ (ethyl acetate). The n.m.r. spectrum showed the following characteristic bands (δ values):
6.8–7.2, 4 aromatic protons
5.3–5.7, 4 olefinic protons
3.6, COOC$\underline{H}_3$

EXAMPLE 4

The process described in Example 1 was repeated, using the appropriate phosphonate reagent, or an equivalent phosphorane $R^4CH_2.CO.CH:PPh_3$ to give the compounds shown below. The products were identified by n.m.r. spectroscopy and are characterised below either by $R_F$ value on thin layer chromatography, or by accurate mass measurement by mass spectrometry of the molecular ion of the appropriate fully protected (trimethylsilyl) derivative, which is prepared by adding, to the compound to be mass measured, bis-trimethylsilyltrifluoroacetamide containing 1% trimethylchlorosilane (Regisiltrade mark) and leaving the mixture for 1 hour. In some cases, the phosphonate reagent, or the unsaturated ketone intermediate have been characterised and appropriate data for these compounds are also given.

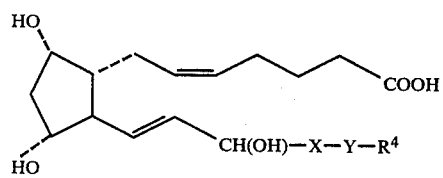

| No. | R⁴ | X | Y | Other substituents in prostanoic acid |
|---|---|---|---|---|
| 21 | phenyl | —CH₂— | —N(CH₃)— | — |
| 22 | 4-chlorophenyl | —C(CH₃)₂— | —O— | — |
| 23 | 4-chlorophenyl | —CH₂— | —S— | — |
| 24 | 3-fluorophenyl | —CH₂— | —O— | — |
| 25 | 2-fluorophenyl | —CH₂— | —O— | — |
| 26 | 3,4-dichlorophenyl | —CH₂— | —O— | — |
| 27 | 2,5-dichlorophenyl | —CH₂— | —O— | — |
| 28 | 2-tolyl | —CH₂— | —O— | — |
| 29 | 2,3-xylyl | —CH₂— | —O— | — |
| 30 | 3,5-xylyl | —CH₂— | —O— | — |
| 31 | 2-chloro-4-methylphenyl | —CH₂— | —O— | — |
| 32 | 3-dimethylaminophenyl | —CH₂— | —O— | — |
| 33 | 1-naphthyl | —CH₂— | —O— | — |
| 34 | 4-chloro-1-naphthyl | —CH₂— | —O— | — |
| 35 | 2-naphthyl | —CH₂— | —O— | — |
| 36 | 6-methyl-2-naphthyl | —CH₂— | —O— | 2-methyl |
| 37 | 6-methoxy-2-naphthyl | —CH₂— | —O— | — |
| 38 | 3-chlorophenyl | —CH₂— | —O— | 2-methyl |
| 39 | 2,3-dichlorophenyl | —CH₂— | —O— | — |
| 40 | 2,6-dichlorophenyl | —CH₂— | —O— | — |
| 41 | 3,5-dichlorophenyl | —CH₂— | —O— | — |
| 42 | 4-chloro-3-methylphenyl | —CH₂— | —O— | — |
| 43 | 3-methoxyphenyl | —CH₂— | —O— | — |
| 44 | 1-chloro-2-naphthyl | —CH₂— | —O— | — |
| 45 | 5,6,7,8-tetrahydro-2-naphthyl | —CH₂— | —O— | — |

| No. | Isomer (a) | Mass spectrum Found | Mass spectrum Calculated | Phosphonate b.p. (°C./mm.) | Enone m.p. (°C.) |
|---|---|---|---|---|---|
| 21 | mp | M⁺ = 691.3994 | 691.3940 | (b) | 145–150 |
|    | lp | 691 | | | |
| 22 | mp | M—CH₃⁺ = 725.3302 | 725.3313 | 150/0.05 | (c) |
|    | lp | | | | |
| 23 | mp | M⁺ = 728.2977 | 728.3006 | (b) | 135–138 |
|    | lp | | | | |
| 24 | mp | M⁺ = 696.3496 | 696.3531 | (d) | 138–139 |
|    | lp | 696 | | | |
| 25 | mp | M⁺ = 696.3510 | 696.3531 | (e) | 144 |
|    | lp | 696 | | | |
| 26 | mp | M⁺ = 746.2791 | 746.2844 | (f) | 150–152 |
|    | lp | 746 | | | |
| 27 | mp | M⁺ = 746.2799 | 746.2844 | (g) | 187–190 |
|    | lp | 746 | | | |
| 28 | mp | M⁺ = 692.3813 | 692.3781 | 154–160/0.05 | 165–167 |
|    | lp | 692 | | | |
| 29 | mp | M⁺ = 706.3971 | 706.3935 | 180/0.15 | 166–168 |
|    | lp | 706 | | | |
| 30 | mp | M⁺ = 706.3922 | 706.3935 | — | 140–142 |
|    | lp | 706 | | | |
| 31 | mp | M⁺ = 726 | 726 | — | 113–115 |
|    | lp | 726 | | | |
| 32 | mp | M⁺ = 721.4020 | 721.4047 | (b) | 138–145 |
|    | lp | 721 | | | |
| 33 | mp | M⁺ = 728.3830 | 728.3781 | (h) | 185–187 |
|    | lp | 728 | | | |
| 34 | mp | M⁺ = 762.3356 | 762.3388 | (i) | (j) |
|    | lp | 762 | | | |
| 35 | mp | M⁺ = 742.3946 | 742.3937 | m.p. 85–86 | 185–187 |
|    | lp | 742 | | | |
| 36 | mp | M⁺ = 742.3902 | 742.3937 | m.p. 71–72 | 153 |
|    | lp | 742 | | | |
| 37 | mp | M⁺ = 758.3910 | 758.3887 | m.p. 58–59 | 195 |
|    | lp | 758 | | | |
| 38 | mp | M⁺ = 726.3346 | 726.3391 | 180/0.2 | (k) |
|    | lp | 726 | | | |
| 39 | mp | M⁺—CH₃ = 731.2644 | 731.2609 | 175/0.03 | 153–155 |
|    | lp | M⁺—CH₃ = 731 | | | |
| 40 | mp | M⁺ = 746.2844 | 746.2844 | m.p. 89–90 | 140–142 |
|    | lp | 746 | | | |
| 41 | mp | M⁺ = 746.2829 | 746.2844 | m.p. 80–82 | 138–139 |

-continued

| No. | Isomer (a) | Mass spectrum Found | Mass spectrum Calculated | Phosphonate b.p. (°C./mm.) | Enone m.p. (°C.) |
|---|---|---|---|---|---|
| 42 | lp mp | 746 M+ = 726.3397 | 726.3391 | — | 143 |
| 43 | lp mp | 726 M+ = 708.3745 | 708.3730 | (l) | 129–130 |
| 44 | lp mixed | 708 M+ = 762.3402 | 762.3391 | m.p. 61–62 | 195 |
| 45 |  mp (m) lp (n) | | | | |

(a) mp = more polar, lp = less polar.
(b) these compounds synthesised from phosphoranes (not phosphonates), made as described below.
(c) $R_F$ = 0.5 (50% ethyl acetate in toluene).
(d) $R_F$ = 0.2 (40% ethyl acetate in methylene dichloride)
(e) $R_F$ = 0.4 (5% acetic acid in ethyl acetate)
(f) $R_F$ = 0.3 (50% ethyl acetate in chloroform)
(g) $R_F$ = 0.23 (50% ethyl acetate in chloroform)
(h) $R_F$ = 0.3 (50% ethyl acetate in methylene dichloride)
(i) $R_F$ = 0.4 (10% methanol in ethyl acetate)
(j) $R_F$ = 0.8 (50% ethyl acetate in toluene)
(k) $R_F$ = 0.6 (50% ethyl acetate in toluene)
(l) $R_F$ = 0.4 (50% ethyl acetate in methylene dichloride)
(m) $R_F$ = 0.25 (3% acetic acid in ethyl acetate)
(n) $R_F$ = 0.30 (3% acetic acid in ethyl acetate)
(m) and (n); δ6.8 (1H, aromatic), 6.6 (2H, aromatic), 5.4 (2H, olefinic) and 5.7 (2H, olefinic).

The preparation of a phosphorane, which may be used in place of a phosphonate in the preparation of a cyclopentane derivative of the invention, is exemplified by the preparation of [3-(3-dimethylaminophenoxy)-acetonylidene]-triphenylphosphorane as follows:

n-Butyl-lithium (3.85 ml. of a 1.3 M solution in hexane) was added to a solution of 3-dimethylaminophenol (685 mg.) in dimethoxyethane (20 ml.) at −70° C. under an atmosphere of nitrogen. The solution was allowed to warm to room temperature, a solution of 3-iodoacetonylidene-triphenylphosphorane (2.22 g.) in benzene (100 ml.) was added, and the mixture was heated under reflux for 2 hours. The mixture was then diluted with toluene (100 ml.), washed with water (2×50 ml.) and dried, the solvents were evaporated and the residue was triturated with ether to give [3-(3-dimethylaminophenoxy)acetonylidene]triphenylphosphorane, m.p. 110°–115° C.

In a similar manner were prepared the analogous N-methylanilino (gum) and 4-chlorophenylthio (m.p. 158°–165° C.) phosphoranes.

EXAMPLE 5

The process described in Example 3 was repeated, using the appropriate more polar C-15 epimer, in place of the more polar C-15 epimer of 16-(4-chlorophenoxy)-9α,11α,15-trihydroxy-17,18,19,20-tetranor-5-cis-13-trans-prostadienoic acid, to give the following methyl esters as single C-15 epimers:

(a) methyl 16-(4-fluorophenoxy)-9α,11α,15-trihydroxy-17,18,19,20-tetranor-5-cis-13-trans-prostadienoate, $R_F$=0.3 (5% methanol in toluene) δ=6.8–7.2 (aromatic), 5.3–5.7 (4 olefinic protons), 3.6 (methyl ester).

(b) methyl 9α,11α,15-trihydroxy-16-(2-naphthyloxy)-17,18,19,20-tetranor-5-cis-13-trans-prostadienoate, M+ =670.3542 (calculated 670.3541).

(c) methyl 9α,11α,15-trihydroxy-2-methyl-16-(2-naphthyloxy)-17,18,19,20-tetranor-5-cis-13-trans-prostadienoate, M+ =684.3678 (calculated 684.3697).

(d) methyl 9α,11α,15-trihydroxy-16-(6-methyl-2-naphthyloxy)-17,18,19,20-tetranor-5-cis-13-trans-prostadienoate, M+ =684.3739 (calculated 684.3698).

(e) methyl 9α,11α,15-trihydroxy-16-(6-methoxy-2-naphthyloxy)-17,18,19,20-tetranor-5-cis-13-trans-prostadienoate, M+ =700.3681 (calculated 700.3647).

(f) methyl 16-(3-chlorophenoxy)-9α,11α,15-trihydroxy-17,18,19,20-tetranor-5-cis-13-trans-prostadienoate, $R_F$=0.3 (ethyl acetate), M+ =654.2973 (calculated 654.2995).

(g) methyl 9α,11α, 15-trihydroxy-2-methyl-16-(3-chlorophenoxy)-17,18,19,20-tetranor-5-cis-13-trans-prostadienoate, $R_F$=0.4 (ethyl acetate), M+ =668.3133 (calculated 668.3151).

EXAMPLE 6

16-(4-Chlorophenoxy)-9α,11α,15-trihydroxy-17,18,19,20-tetranor-5-cis-13-trans-prostanoic acid (20 mg. of the more polar C-15 epimer) was treated with an excess of dilute aqueous ammonia to form the ammonium salt. The excess of ammonia was evaporated under reduced pressure, and the residue was treated with the stoichiometric amount of silver nitrate to form the silver salt. The silver salt was filtered off, dried, dissolved in n-butyl iodide (0.5 ml.) and stirred at room temperature for 1 hour. The solution was extracted with ethyl acetate, the ethyl acetate extract was evaporated to dryness, and the residue was chromatographed on Florisil (1 g.) using 50% ethyl acetate in toluene as eluant, to give n-butyl 16-(4-chlorophenyl)-9α,11α,15-trihydroxy-17,18,19,20-tetranor-5-cis-13-trans-prostadienoate, M+ =696.3427 (calculated 696.3464), $R_F$=0.4 (ethyl acetate).

In a similar manner, but using ethyl iodide in place of n-butyl iodide, there was obtained ethyl 16-(4-chlorophenyl)-9α,11α,15-trihydroxy-17,18,19,20-tetranor-5-cis-13-trans-prostadienoate, M+ =668.3086 (calculated 668.3151).

EXAMPLE 7

A solution of the mixed anhydride of acetic acid and the more polar C-15 epimer of 9α-acetoxy-16-(4-chlorophenoxy)-11α,16-bis(tetrahydropyran-2-yloxy)-17,18,19,20-tetranor-5-cis-13-trans-prostadienoic acid (73 mg.) in 2 ml. of a 2:1 mixture of acetic acid and water, was stirred at 47° C. under nitrogen for 4 hours. The solvents were evaporated, the residue was dissolved in dilute aqueous sodium bicarbonate solution (2 ml.) and the solution was extracted with ethyl acetate (3×2 ml.). The extracts were discarded, the aqueous solution was acidified to pH 3–4 with 2 N aqueous oxalic acid and the acidified solution was extracted with ethyl acetate (4×5 ml.). The ethyl acetate extracts were washed with a 1:1 mixture of saturated brine and water, and were then dried. After evaporation of the ethyl acetate, the residue was purified by thin-layer chromatography on silica gel using 3% acetic acid in ethyl acetate, to give the more polar C-15 epimer of 9α-acetoxy-16-(4-chlorophenoxy)-11α,15-dihydroxy-17,18,19,20-tetranor-5-cis-13-trans-prostadienoic acid, $M^+ = 682.2942$ (calculated 682.2944).

The bis-tetrahydropyranyl ether used as starting material may be prepared as follows:

A solution of the more polar C-15 epimer of 9α-hydroxy-16-(4-chlorophenoxy)-11α,15-bis(tetrahydropyran-2-yloxy)-17,18,19,20-tetranor-5-cis-13-trans-prostadienoic acid (70 mg.) in 0.15 ml. of a 2:1 mixture of pyridine and acetic anhydride was kept at room temperature for 16 hours. The volatile material was evaporated and cyclohexane (10 ml.) was added to, and boiled off from, the residue three times, leaving the mixed anhydride of acetic acid and 9α-acetoxy-16-(4-chlorophenoxy)-11α,15-bis(tetrahydropyran-2-yloxy)-17,18,19,20-tetranor-5-cis-13-trans-prostadienoic acid as a yellow oil, $\nu$max (CHCl$_3$) 1720, 1810 cm$^{-1}$.

EXAMPLE 8

To a solution of 9α-acetoxy-16-(4-chlorophenoxy)-11α,15-dihydroxy-17,18,19,20-tetranor-5-cis-13-trans-prostadienoic acid (12 mg.) in methanol (1 ml.) at 0° C. was added an excess of a solution of diazomethane in ether. After 10 minutes, the solvents were evaporated, the residue was dissolved in ether, and the solution was treated with lithium aluminium hydride (50 mg.). The mixture was stirred at room temperature for 1 hour, the excess of hydride was destroyed by the addition of water (1 ml.) and the mixture was extracted with ethyl acetate to give 16-(4-chlorophenoxy)-9α,11α,15-trihydroxy-17,18,19,20-tetranor-5-cis-13-trans-prostadienol, $M^+ = 698.3439$ (calculated 698.3441), $R_F = 0.2$ (ethyl acetate).

In a similar manner, there were obtained: 16-(3-chlorophenoxy)-9α,11α,15-trihydroxy-2-methyl-17,18,19,20-tetranor-5-cis-13-trans-prostadienol, $R_F = 0.15$ (ethyl acetate, $M^+ = 712.3575$ (calculated 712.3597). 9α,11α,15-trihydroxy-16-(6-methyl-2-naphthyloxy)-17,18,19,20-tetranor-5-cis-13-trans-prostadienol, $R_F = 0.2$ (ethyl acetate).

EXAMPLE 9

The process described in Example 1 was repeated using the appropriate phosphonate reagent, to give:

(a) 9α,11α,15-trihydroxy-16-(4-hydroxyphenoxy)-17,18,19,20-tetranor-5-cis-13-trans-prostadienoic acid, $R_F = 0.2$ and 0.3 (3% acetic acid in ethyl acetate). $\delta = 6.82$ (4H, aromatic), 5.3–5.7 (4H, olefinic), 3.98–5.1 (10H, >CH.O— and exchangeable protons); phosphonate, $R_F = 0.2$ (10% methanol in ethyl acetate); enone, m.p. 135°–140° C.

(b) 16-furfuryl-9α,11α,15-trihydroxy-17,18,19,20-tetranor-5-cis-13-trans-prostadienoic acid, $R_F = 0.5$ (3% acetic acid in ethyl acetate), $\delta = 7.5$ (1H) and 6.3 (2H) (furyl protons) 5.1–5.6 (4H, olefinic); phosphonate, b.p. 200° C./0.2 mm; enone, m.p. 92°–93° C.

(c) 16-(3-allylphenoxy)-9α,11α,15-trihydroxy-17,18,19,20-tetranor-5-cis-13-trans-prostadienoic acid, $M^+ = 718.3892$ (calculated 718.3938); phosphonate, $R_F = 0.32$ (ethyl acetate); enone, m.p. 110°–112° C.

EXAMPLE 10

The process described in Example 1 was repeated, using a 9-oxo prostanoic acid derivative in place of a 9α-hydroxy prostanoic acid derivative, to give the compounds shown below. For measurement of mass spectra, the acids were converted to methyl esters with diazomethane, the 9-oxo group was protected by conversion to the methoxime with methoxyamine, and, where indicated, the hydroxy groups at C-11 and C-15 were protected as the trimethylsilyl derivatives. N.m.r. spectra were measured in deuterated acetone.

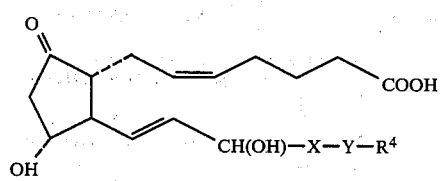

| No. | R$^4$ | X | Y |
|---|---|---|---|
| 46 | phenyl | —CH$_2$— | —O— |
| 47 | phenyl | —CH(CH$_3$)— | —O— |
| 48 | phenyl | —(CH$_2$)$_3$— | —O— |
| 49 | 1-naphthyl | —CH$_2$— | —O— |
| 50 | 2-naphthyl | —CH$_2$— | —O— |
| 51 | 4-chlorophenyl | —CH$_2$— | —O— |
| 52 | 4-chlorophenyl | —CH$_2$— | —S— |
| 53 | 3-chlorophenyl | —CH$_2$— | —O— |
| 54 | 2-chlorophenyl | —CH$_2$— | —O— |
| 55 | 4-chlorophenyl | —C(CH$_3$)$_2$— | —O— |
| 56 | 4-bromophenyl | —CH$_2$— | —O— |
| 57 | 4-fluorophenyl | —CH$_2$— | —O— |
| 58 | 3-fluorophenyl | —CH$_2$— | —O— |
| 59 | 2-fluorophenyl | —CH$_2$— | —O— |
| 60 | 2,4-dichlorophenyl | —CH$_2$— | —O— |
| 61 | 2,5-dichlorophenyl | —CH$_2$— | —O— |
| 62 | 3,5-dichlorophenyl | —CH$_2$— | —O— |
| 63 | 4-tolyl | —CH$_2$— | —O— |
| 64 | 3-tolyl | —CH$_2$— | —O— |
| 65 | 2-tolyl | —CH$_2$— | —O— |
| 66 | 3,5-xylyl | —CH$_2$— | —O— |
| 67 | 4-chloro-3-methylphenyl | —CH$_2$— | —O— |
| 68 | 2-chloro-4-methylphenyl | —CH$_2$— | —O— |
| 69 | 3-trifluoromethylphenyl | —CH$_2$— | —O— |
| 70 | 4-methoxyphenyl | —CH$_2$— | —O— |
| 71 | 2-methoxyphenyl | —CH$_2$— | —O— |
| 72 | 4-chloro-1-naphthyl | —CH$_2$— | —O— |

| No. | Isomer* | Characterising Data |
|---|---|---|
| 46 | mixed | $R_F = 0.2$ (acetone/cyclohexane/ethyl acetate - 1:2:2) N.m.r.: δ6.98–7.28 (5H, aromatic), 5.48 (2H, cis olefin), 5.78 (2H, trans olefin), 3.5–4.5 (5H, >CH.O— and —COOH) |
| 47 | mixed | $M^+ = 589.3267$ [calculated 589.3255 for methyl ester, 9-methoxime, 11,15-di-(trimethylsilyl) derivative]. $R_F = 0.4$ (3% acetic acid in ethyl acetate) |
| 48 | mixed | $R_F = 0.3$ (3% acetic acid in ethyl acetate) |
| 49 | mixed | $R_F = 0.4$ (3% acetic acid in ethyl acetate). |

-continued

| No. | Isomer* | Characterising Data |
|---|---|---|
|  |  | N.m.r.: aromatic protons at δ8.3–8.5 (1H), 7.7–7.9 (1H), 7.2–7.5 (4H) and 6.8–7.08 (1H) |
| 50 | mixed | $R_F$ = 0.3 (3% acetic acid in ethyl acetate). N.m.r.: aromatic protons at δ7.7–7.8 (3H) and 7.1–7.5 (4H) |
| 51 | mp | M+ = 609.2633 [calculated 609.2709 for methyl ester, 9-methoxime, 11,15-di(trimethylsilyl) derivative]. $R_F$ = 0.4 (3% acetic acid in ethyl acetate) |
| 52 | mixed | $R_F$ = 0.5 (3% acetic acid in ethyl acetate). N.m.r.: aromatic protons at δ7.3 (4H) |
| 53 | mp | $R_F$ = 0.3 (3% acetic acid in ethyl acetate). N.m.r.: aromatic protons at δ7.15 (1H) and 6.9 (3H) |
| 54 | mixed | $R_F$ = 0.4 (3% acetic acid in ethyl acetate) |
| 55 | mixed | $R_F$ = 0.5 (3% acetic acid in ethyl acetate). N.m.r.: aromatic protons at δ7.28 (2H), 7.19 (2H) and 2 methyls at δ1.25 and 1.30 (6H) |
| 56 | mixed | M+ = 509.1417 (calculated 509.1413 for methyl ester, 9-methoxime) |
| 57 | mixed | $R_F$ = 0.3 (3% acetic acid in ethyl acetate) N.m.r.: aromatic protons at δ6.91 (2H) and 7.08 (2H) |
| 58 | mixed | $R_F$ = 0.3 (2% acetic acid in ethyl acetate). N.m.r.: aromatic protons at δ7.25 (1H) and 6.65 (3H) |
| 59 | mixed | $R_F$ = 0.4 (5% acetic acid in ethyl acetate). N.m.r.: aromatic protons at δ7.05 (4H) |
| 60 | mixed | $R_F$ = 0.4 (0.25% acetic acid in ethyl acetate) N.m.r.: aromatic protons at δ7.12 (1H), 7.3 (1H) and 7.41 (1H) |
| 61 | mixed | $R_F$ = 0.34 (3% acetic acid in ethyl acetate). N.m.r.: aromatic protons at δ7.3 (1H), 7.15 (1H) and 6.9 (1H) |
| 62 | mixed | $R_F$ = 0.34 (3% acetic acid in ethyl acetate). N.m.r.: aromatic protons at δ6.9 (3H) |
| 63 | mixed | $R_F$ = 0.2 (cyclohexane/ethyl acetate/acetone, 2:2:1). N.m.r.: aromatic protons at δ6.7 (2H) and 7.1 (2H), and methyl at δ2.28 |
| 64 | mixed | $R_F$ = 0.5 (3% acetic acid in ethyl acetate). N.m.r.: aromatic protons at δ7.05 (1H) and 6.73 (3H), and methyl at δ2.28 |
| 65 | mixed | M+ = 589.3284 [calculated 589.3254 for methyl ester, methoxime, di(trimethylsilyl) derivative]. $R_F$ = 0.35 (3% acetic acid in ethyl acetate) |
| 66 | mixed | $R_F$ = 0.2 (cyclohexane/acetone/ethyl acetate - 4:1:2). N.m.r.: aromatic protons at δ6.5 (3H), and methyls (6H) at 2.28 |
| 67 | mixed | $R_F$ = 0.5 (5% acetic acid in ethyl acetate). N.m.r.: aromatic protons at δ7.2 (1H) and 6.85 (2H), and methyl at 2.3 |
| 68 | mixed | $R_F$ = 0.4 (cyclohexane/ethyl acetate/acetone - 4:2:1). N.m.r.: aromatic protons at δ7.18 (1H) and 6.80 (2H), and methyl at 2.2 |
| 69 | mp | $R_F$ = 0.5 (5% acetic acid in ethyl acetate). N.m.r.: aromatic protons at δ7.5 (1H) and 7.25 (3H) |
| 70 | mixed | $R_F$ = 0.6 (3% acetic acid in ethyl acetate) |
| 71 | mixed | $R_F$ = 0.65 and 0.7 (3% acetic acid in ethyl acetate) |
| 72 | mixed | $R_F$ = 0.4 (3% acetic acid in ethyl acetate). N.m.r.: aromatic protons at δ8.4 (1H), 8.15 (1H), 7.6 (3H) and 7.08 (1H) |

*mp = more polar.

The 9-oxo prostanoic acid derivatives used as starting materials may be obtained by oxidation of the corresponding 9α-hydroxy compound, as exemplified below for the preparation of 9-oxo-16-phenoxy-11α,15-bis(tetrahydropyran-2-yloxy)-17,18,19,20-tetranor-5-cis-13-trans-prostadienoic acid:

To a solution of 9α-hydroxy-16-phenoxy-11α,15-bis(-tetrahydropyran-2-yloxy)-17,18,19,20-tetranor-5-cis-13-trans-prostadienoic acid (270 mg.) in acetone (5 ml.) at −10° C. was added Jones' reagent (chromic acid in acetone), (0.163 ml.). After 15 minutes, isopropanol (1 drop) was added, followed by ethyl acetate (20 ml.). The solution was washed with 1:1 saturated brine/water, and was dried. Evaporation of the solvents, and chromatography of the residue on silica, using 1:1 ether/petroleum ether (b.p. 40°–60° C.) as eluting solvent, gave the required 9-oxo-bis(tetrahydropyranyl ether), $R_F$=0.2 (50% ethyl acetate in toluene).

EXAMPLE 11

The process described in Example 3 was repeated, using 11α,15-dihydroxy-16-(2-naphthyloxy)-9-oxo-17,18,19,20-tetranor-5-cis-13-trans-prostadienoic acid, in place of 16-(4-chlorophenoxy)-9α,11α,15-trihydroxy-17,18,19,20-tetranor-5-cis-13-trans-prostadienoic acid, to give methyl 11α,15-dihydroxy-16-(2-naphthyloxy)-9-oxo-17,18,19,20-tetranor-5-cis-13-trans-prostadienoate, $R_F$=0.3 (ethyl acetate).

EXAMPLE 12

To a solution of 16-(4-chlorophenylthio)-9α,11α,15-trihydroxy-17,18,19,20-tetranor-5-cis-13-trans-prostadienoic acid (12 mg.) in methanol (0.5 ml) at 0° C. was added a solution of sodium periodate (5 mg.) in water (0.5 ml.). After 18 hours the solvents were evaporated, and the residue was extracted with acetone to give 16-(4-chlorophenylsulphinyl)-9α,11α,15-trihydroxy-17,18,19,20-tetranor-5-cis-13-trans-prostadienoic acid, M+=744.2918 (calculated 744.2956), $R_F$=0.2 (3% acetic acid in ethyl acetate).

EXAMPLE 13

|  | % w/v |
|---|---|
| 16-(4-fluorophenoxy)-9α,11α,15-trihydroxy-17,18,19,20-tetranor-5-cis-13-trans-prostadienoic acid | 0.003 |
| Sodium phosphate | 2.90 |
| Sodium hydrogen phosphate | 0.30 |
| Water for injection | to 100 |

The sodium phosphate was dissolved in about 80% of the water, followed by the prostadienoic acid derivative, and, when dissolved, the sodium hydrogen phosphate. The solution was made up to volume with water for injection, and the pH was checked to be between 6.7 and 7.7. The solution was filtered to remove particulate matter, sterilised by filtration, and filled into presterilised neutral glass ampoules under aseptic conditions. Immediately before use, the contents of an ampoule are diluted in sodium chloride B.P. for administration by intravenous infusion.

The prostadienoic acid derivative may, of course, be replaced by an equivalent amount of another prostanoic acid derivative of the invention.

What we claim is:

1. A method of inducing luteolysis in a host requiring such treatment, comprising administering to said host a luteolytically-effective amount of a prostanoic acid derivative of the formula:

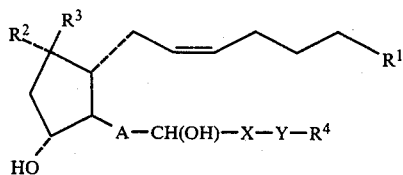

wherein $R^1$ is carboxy or alkoxycarbonyl of up to 11 carbon atoms, $R^2$ is hydroxy or alkanoyloxy of 1 to 4 carbon atoms; $R^3$ is hydrogen; A is trans-vinylene; X is alkylene of 1 to 3 carbon atoms bearing as substituents 0, 1 or 2 alkyls each of 1 to 3 carbon atoms; Y is oxygen; and $R^4$ is phenyl or naphthyl which is unsubstituted or is substituted by 1 or 2 substituents selected from halogen, alkyl of 1 to 4 carbon atoms and trifluoromethyl; and wherein said derivative has 0 to 1 alkyl group of up to 4 carbon atoms on carbon atom 2, 3 or 4, or for those derivatives wherein $R^1$ is carboxy, a pharmaceutically-acceptable salt thereof.

2. A method according to claim 1 wherein the prostanoic acid derivative is 16-(3-chlorophenoxy)-9α,1α,15-trihydroxy-17,18,19,20-tetranor-5-cis-13-trans-prostadienoic acid.

3. A method according to claim 1 wherein the prostanoic acid derivative is 9α,11α,15-trihydroxy-16-(3-trifluoromethylphenoxy)-17,18,19,20-tetranor-5-cis-13-trans-prostadienoic acid.

4. A method of inducing luteolysis in a host requiring such treatment comprising administering to said host a luteolytically-effective amount of a prostanoic acid derivative of the formula

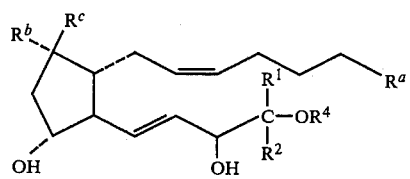

wherein $R^a$ is carboxy or alkoxycarbonyl of up to 11 carbon atoms; $R^b$ is hydroxy or alkanoyloxy of 1 to 4 carbon atoms; $R^c$ is hydrogen; $R^1$ and $R^2$ are hydrogen or lower alkyl and $R^4$ is phenyl, naphthyl or monosubstituted phenyl wherein said substituent is halo, trifluoromethyl, phenyl, lower alkyl or lower alkoxy.

* * * * *